(12) United States Patent
Jennings et al.

(10) Patent No.: US 8,377,108 B2
(45) Date of Patent: Feb. 19, 2013

(54) STAGGERED TWO BALLOON BIFURCATION CATHETER ASSEMBLY AND METHODS

(75) Inventors: Adam Jennings, Buffalo, MN (US); Mark Sagedahl, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 586 days.

(21) Appl. No.: 12/131,532

(22) Filed: Jun. 2, 2008

(65) Prior Publication Data
US 2009/0299454 A1 Dec. 3, 2009

(51) Int. Cl.
*A61F 2/06* (2006.01)
(52) U.S. Cl. ..................................................... 623/1.11
(58) Field of Classification Search ............... 604/96.01, 604/101.01–101.05, 284; 606/108, 153, 606/191–192, 194–195, 198; 623/1.11–1.12, 623/1.23, 1.35
See application file for complete search history.

(56) References Cited

U.S. PATENT DOCUMENTS

| | | |
|---|---|---|
| 1,596,754 A | 8/1926 | Moschelle |
| 3,657,744 A | 4/1972 | Ersek |
| 3,872,893 A | 3/1975 | Roberts |
| 3,884,242 A | 5/1975 | Bazell et al. |
| 4,140,126 A | 2/1979 | Choudhury |
| 4,309,994 A | 1/1982 | Grunwald |
| 4,385,631 A | 5/1983 | Uthmann |
| 4,410,476 A | 10/1983 | Redding et al. |
| 4,413,989 A | 11/1983 | Schjeldahl et al. |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |

(Continued)

FOREIGN PATENT DOCUMENTS

| | | |
|---|---|---|
| CA | 2227446 | 12/1997 |
| CA | 2318314 | 7/1999 |

(Continued)

OTHER PUBLICATIONS

Caputo et al., "Stent Jail: A Minimum-Security Prison," The American Journal of Cardiology, vol. 77, pp. 1226-1230, Jun. 1, 1996.

(Continued)

*Primary Examiner* — Ryan Severson
*Assistant Examiner* — Ashley Cronin
(74) *Attorney, Agent, or Firm* — Seager, Tufte & Wickhem, LLC

(57) ABSTRACT

A catheter assembly and related methods directed to stent delivery systems that include a stent and a catheter assembly having first and second balloons. The stent includes a side branch aperture and expandable structure defining the side branch aperture. The expandable structure is configured to move into a radial outward orientation relative to a sidewall of the stent. The portions of the first and second balloons are positioned within the stent in a generally coaxial arrangement with the first balloon extending distally from the distal open end of the stent and the second balloon extending proximally from the proximal open end of the stent. The expandable structure of the stent is moved towards the radial outward orientation by advancing the second balloon at least partially distally through the side branch aperture. In some arrangements, the second balloon is at least partially inflated when advanced through the side branch aperture.

17 Claims, 7 Drawing Sheets

U.S. PATENT DOCUMENTS

| | | |
|---|---|---|
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,029 A | 9/1988 | Patel |
| 4,774,949 A | 10/1988 | Fogarty |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,950,227 A | 8/1990 | Savin et al. |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,170 A | 10/1991 | Cameron |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang et al. |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,244,619 A | 9/1993 | Burnham |
| 5,254,619 A | 10/1993 | Ando |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Cardon et al. |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,201 A | 10/1996 | Burns |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Marcade |
| 5,676,697 A | 10/1997 | McDonald |
| 5,679,400 A | 10/1997 | Tuch |
| 5,681,345 A | 10/1997 | Euteneuer |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon et al. |
| 5,709,713 A | 1/1998 | Evans |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |

| Patent No. | Date | Name |
|---|---|---|
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,788,707 A | 8/1998 | Del Toro et al. |
| 5,792,105 A | 8/1998 | Lin et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane et al. |
| 5,938,696 A | 8/1999 | Goicoechea et al. |
| 5,948,016 A | 9/1999 | Jang |
| 5,951,599 A | 9/1999 | McCrory |
| 5,961,490 A | 10/1999 | Adams |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,015,431 A | 1/2000 | Thornton et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,166 A | 5/2000 | Bischoff et al. |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,045 A | 8/2000 | Del Toro et al. |
| 6,096,073 A | 8/2000 | Webster et al. |
| 6,099,497 A | 8/2000 | Adams et al. |
| 6,102,938 A | 8/2000 | Evans et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,143,002 A | 11/2000 | Vietmeier |
| 6,146,356 A | 11/2000 | Wang et al. |
| 6,152,945 A | 11/2000 | Bachinski et al. |
| 6,159,187 A | 12/2000 | Park et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,353 B1 | 2/2001 | Makower et al. |
| 6,190,403 B1 | 2/2001 | Fischell et al. |
| 6,193,746 B1 | 2/2001 | Strecker |
| 6,203,568 B1 | 3/2001 | Lombardi et al. |
| 6,203,569 B1 | 3/2001 | Wijay |
| 6,210,380 B1 | 4/2001 | Mauch |
| 6,210,429 B1 | 4/2001 | Vardi et al. |
| 6,210,431 B1 | 4/2001 | Power |
| 6,210,481 B1 | 4/2001 | Sakai et al. |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,097 B1 | 4/2001 | Wang et al. |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,251,133 B1 | 6/2001 | Richter et al. |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,258,534 B1 | 7/2001 | Lugharn, Jr. et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,277 B1 | 9/2001 | Yan |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,319,275 B1 | 11/2001 | Lashinski et al. |
| 6,325,821 B1 | 12/2001 | Gaschino et al. |
| 6,325,826 B1 | 12/2001 | Vardi et al. |
| 6,331,186 B1 | 12/2001 | Wang et al. |
| 6,334,870 B1 | 1/2002 | Ehr et al. |
| 6,342,066 B1 | 1/2002 | Toro et al. |
| 6,346,089 B1 | 2/2002 | Dibie |
| 6,350,277 B1 | 2/2002 | Kocur |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,558 B1 | 3/2002 | Hieshima et al. |
| 6,371,978 B1 | 4/2002 | Wilson |
| 6,379,372 B1 | 4/2002 | Dehashtian et al. |
| 6,383,213 B2 | 5/2002 | Wilson et al. |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |

| | | |
|---|---|---|
| 6,428,567 B2 | 8/2002 | Wilson et al. |
| 6,428,570 B1 | 8/2002 | Globerman |
| 6,432,133 B1 | 8/2002 | Lau et al. |
| 6,436,090 B1 | 8/2002 | Sanchez et al. |
| 6,436,104 B2 | 8/2002 | Hojeibane |
| 6,436,134 B2 | 8/2002 | Richter et al. |
| 6,440,161 B1 | 8/2002 | Madrid et al. |
| 6,443,880 B2 | 9/2002 | Blais et al. |
| 6,445,166 B2 | 9/2002 | Nishiyama |
| 6,468,302 B2 | 10/2002 | Cox et al. |
| 6,475,208 B2 | 11/2002 | Mauch |
| 6,478,814 B2 | 11/2002 | Wang et al. |
| 6,478,816 B1 | 11/2002 | Kveen et al. |
| 6,482,211 B1 | 11/2002 | Choi |
| 6,485,511 B2 | 11/2002 | Lau et al. |
| 6,488,694 B1 | 12/2002 | Lau et al. |
| 6,494,875 B1 | 12/2002 | Mauch |
| 6,494,905 B1 | 12/2002 | Zedler et al. |
| 6,508,836 B2 | 1/2003 | Wilson et al. |
| 6,511,504 B1 | 1/2003 | Lau et al. |
| 6,511,505 B2 | 1/2003 | Cox et al. |
| 6,514,281 B1 | 2/2003 | Blaesser et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,572,647 B1 | 6/2003 | Supper et al. |
| 6,576,009 B2 | 6/2003 | Ryan et al. |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. |
| 6,596,022 B2 | 7/2003 | Lau et al. |
| 6,599,315 B2 | 7/2003 | Wilson |
| 6,599,316 B2 | 7/2003 | Vardi et al. |
| 6,602,284 B2 | 8/2003 | Cox et al. |
| 6,641,609 B2 | 11/2003 | Globerman |
| 6,645,241 B1 | 11/2003 | Strecker |
| 6,652,573 B2 | 11/2003 | von Oepen |
| 6,669,717 B2 | 12/2003 | Marotta et al. |
| 6,676,667 B2 | 1/2004 | Mareiro et al. |
| 6,679,911 B2 | 1/2004 | Burgermeister |
| 6,682,536 B2 | 1/2004 | Vardi et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,440 B2 | 3/2004 | Matin et al. |
| 6,736,841 B2 | 5/2004 | Musbach et al. |
| 6,746,411 B2 | 6/2004 | Khaw |
| 6,770,092 B2 | 8/2004 | Richter |
| 6,780,174 B2 | 8/2004 | Mauch |
| 6,802,856 B2 | 10/2004 | Wilson |
| 6,827,735 B2 | 12/2004 | Greenberg |
| 6,827,736 B2 | 12/2004 | Perouse |
| 6,843,803 B2 | 1/2005 | Ryan et al. |
| 6,852,124 B2 | 2/2005 | Cox et al. |
| 6,855,125 B2 | 2/2005 | Shanley |
| 6,884,258 B2 | 4/2005 | Vardi et al. |
| 6,890,349 B2 | 5/2005 | McGuckin, Jr. et al. |
| 6,896,699 B2 | 5/2005 | Wilson et al. |
| 6,905,477 B2 | 6/2005 | McDonnell et al. |
| 6,908,477 B2 | 6/2005 | McGuckin, Jr. et al. |
| 6,939,368 B2 | 9/2005 | Simso |
| 6,942,689 B2 | 9/2005 | Majercak |
| 6,955,687 B2 | 10/2005 | Richter et al. |
| 6,955,688 B2 | 10/2005 | Wilson et al. |
| 6,962,602 B2 | 11/2005 | Vardi et al. |
| 6,980,174 B2 | 12/2005 | Flasza et al. |
| 7,018,400 B2 | 3/2006 | Lashinski et al. |
| 7,056,323 B2 | 6/2006 | Mareiro et al. |
| 7,105,019 B2 | 9/2006 | Hojeibane |
| 7,118,593 B2 | 10/2006 | Davidson et al. |
| 7,125,419 B2 | 10/2006 | Sequin et al. |
| 7,163,553 B2 | 1/2007 | Limon |
| 7,220,275 B2 | 5/2007 | Davidson et al. |
| 7,238,197 B2 | 7/2007 | Sequin et al. |
| 7,244,853 B2 | 7/2007 | Schreiber et al. |
| 7,252,679 B2 | 8/2007 | Fischell et al. |
| 7,334,557 B2 | 2/2008 | Callan |
| 7,344,514 B2 | 3/2008 | Shanley |
| 7,387,639 B2 | 6/2008 | Bourang et al. |
| 7,476,243 B2 | 1/2009 | Eidenschink |
| 2001/0037146 A1 | 11/2001 | Lau et al. |
| 2001/0039448 A1 | 11/2001 | Dibie |
| 2002/0013618 A1 | 1/2002 | Marotta et al. |
| 2002/0032478 A1 | 3/2002 | Boekstegers et al. |
| 2002/0058990 A1 | 5/2002 | Jang |
| 2002/0123790 A1 | 9/2002 | White et al. |
| 2002/0156516 A1 | 10/2002 | Vardi et al. |
| 2002/0165604 A1 | 11/2002 | Shanley |
| 2002/0193872 A1 | 12/2002 | Trout, III et al. |
| 2002/0193873 A1 | 12/2002 | Brucker et al. |
| 2003/0009209 A1 | 1/2003 | Hojelbane |
| 2003/0009214 A1 | 1/2003 | Shanley |
| 2003/0014102 A1 | 1/2003 | Hong et al. |
| 2003/0125802 A1 | 7/2003 | Callol et al. |
| 2003/0144623 A1 | 7/2003 | Heath et al. |
| 2003/0181923 A1 | 9/2003 | Vardi |
| 2004/0015227 A1 | 1/2004 | Vardi et al. |
| 2004/0049259 A1 | 3/2004 | Strecker |
| 2004/0148006 A1 | 7/2004 | Davidson et al. |
| 2004/0167463 A1 | 8/2004 | Zawacki et al. |
| 2004/0176837 A1 | 9/2004 | Atladottir et al. |
| 2005/0015108 A1 | 1/2005 | Williams et al. |
| 2005/0075722 A1 | 4/2005 | Chuter |
| 2005/0192656 A1* | 9/2005 | Eidenschink ................ 623/1.11 |
| 2005/0209673 A1 | 9/2005 | Shaked |
| 2005/0245941 A1 | 11/2005 | Vardi et al. |
| 2006/0247756 A1 | 11/2006 | Richter |
| 2007/0100301 A1* | 5/2007 | Gumm ........................ 604/284 |
| 2007/0179591 A1 | 8/2007 | Baker et al. |
| 2007/0203562 A1 | 8/2007 | Malewicz et al. |
| 2008/0065141 A1 | 3/2008 | Holman et al. |
| 2008/0086191 A1 | 4/2008 | Valencia et al. |
| 2008/0255581 A1 | 10/2008 | Bourang et al. |
| 2008/0288041 A1 | 11/2008 | Holman et al. |
| 2009/0036830 A1 | 2/2009 | Jablonski et al. |

FOREIGN PATENT DOCUMENTS

| | | |
|---|---|---|
| CA | 2403826 | 9/2001 |
| CA | 2237829 | 11/2006 |
| DE | 9014845.2 | 9/1991 |
| DE | 29701758 | 5/1997 |
| DE | 60036233 | 5/2008 |
| EP | 0515201 | 3/1997 |
| EP | 0891751 | 1/1999 |
| EP | 0897700 | 2/1999 |
| EP | 0904745 | 3/1999 |
| EP | 0965311 | 12/1999 |
| EP | 1031328 | 8/2000 |
| EP | 0698380 | 2/2002 |
| EP | 0884028 | 2/2002 |
| EP | 0705116 | 4/2002 |
| EP | 0646365 | 1/2004 |
| EP | 0684022 | 2/2004 |
| EP | 0897698 | 6/2004 |
| EP | 1182989 | 12/2004 |
| EP | 0551179 | 4/2005 |
| EP | 1157674 | 7/2005 |
| EP | 0804907 | 11/2005 |
| EP | 1031330 | 11/2005 |
| EP | 0876805 | 8/2006 |
| EP | 1512380 | 8/2007 |
| FR | 2678508 | 1/1993 |
| GB | 285530 | 2/1928 |
| JP | 8-299456 | 11/1996 |
| WO | WO 88/06026 | 8/1988 |
| WO | WO 90/13332 | 11/1990 |
| WO | WO 91/12779 | 9/1991 |
| WO | WO 92/14508 | 9/1992 |
| WO | WO 92/19308 | 11/1992 |
| WO | WO 93/04722 | 3/1993 |
| WO | WO 95/08965 | 4/1995 |
| WO | WO 95/21592 | 8/1995 |
| WO | WO 96/29955 | 10/1996 |
| WO | WO 96/34580 | 11/1996 |

| | | |
|---|---|---|
| WO | WO 96/36269 | 11/1996 |
| WO | WO 96/41592 | 12/1996 |
| WO | WO 97/09946 | 3/1997 |
| WO | 9715346 | 5/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 97/46174 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/00835 | 1/1999 |
| WO | WO 99/15103 | 4/1999 |
| WO | WO 99/17680 | 4/1999 |
| WO | WO 99/24104 | 5/1999 |
| WO | WO 99/34749 | 7/1999 |
| WO | WO 99/35979 | 7/1999 |
| WO | WO 99/36002 | 7/1999 |
| WO | WO 99/39661 | 8/1999 |
| WO | WO 99/44539 | 9/1999 |
| WO | WO 99/49793 | 10/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/44307 | 8/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/091951 | 11/2002 |
| WO | WO 02/094336 | 11/2002 |
| WO | WO 03/055414 | 7/2003 |
| WO | WO 2004/026180 | 4/2004 |
| WO | WO 2005/107643 | 11/2005 |
| WO | WO 2006/033126 | 3/2006 |
| WO | WO 2006/124162 | 11/2006 |
| WO | WO 2007/100672 | 9/2007 |

OTHER PUBLICATIONS

Carrie et al., ""T"-Shaped Stent Placement: A Technique for the Treatment of Dissected Bifurcation Lesions," Catheterization and Cardiovascular Diagnosis, vol. 37, pp. 311-313, 1996.

Chevalier et al., "Placement of Coronary Stents in Bifurcation Lesions by the "Culotte" Technique," The American Journal of Cardiology, vol. 82, pp. 943-949, Oct. 15, 1998.

Colombo et al., ""Kissing" Stents for Bifurcational Coronary Lesion," Catheterization and Cardiovascular Diagnosis, vol. 30, pp. 327-330, 1993.

U.S. Appl. No. 08/642,297, filed May 3, 1996, to Richter et al.
U.S. Appl. No. 09/325,996, filed Jun. 4, 1999, to Vardi et al.
U.S. Appl. No. 09/533,616, filed Mar. 22, 2000, to Vardi et al.
U.S. Appl. No. 09/614,472, filed Jul. 11, 2000, to Davidson et al.
U.S. Appl. No. 09/663,111, filed Sep. 15, 2000, to Davidson et al.
U.S. Appl. No. 12/183,163, filed Jul. 31, 2008, to Gunderson.
U.S. Appl. No. 12/183,869, filed Jul. 31, 2008, to Prindle et al.
U.S. Appl. No. 12/183,894, filed Jul. 31, 2008, to Tegels.

Dichek et al., "Seeding of Intravascular Stents with Genetically Engineered Endothelial Cells," Circulation, vol. 80, No. 5, pp. 1347-1353, Nov. 1989.

Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.

Katoh et al., "New Double Wire Technique to Stent Ostial Lesions," Catheterization and Cardiovascular Diagnosis, vol. 40, pp. 400-402, 1997.

Lear et al., "The Northridge Earthquake as a Trigger for Acute Myocardial Infarction," 1 page, 1996.

Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.

Nakamura et al., "Techniques for Palmaz-Schatz Stent Deployment in Lesions with a Large Side Branch," Catheterization and Cardiovascular Diagnosis, vol. 34, pp. 353-361, 1995.

Satler et al. "Bifurcation Disease: To Treat or Not to Treat," Catheterization and Cardiovascular Interventions, vol. 50, pp. 411-412, 2000.

SCIMED Life Systems, Inc., "TRIO 14 PTCA Catheter, Re-Engineering Over-The-Wire Balloon Technology," Brochure, 4 pages, 1994.

Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.

Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

* cited by examiner

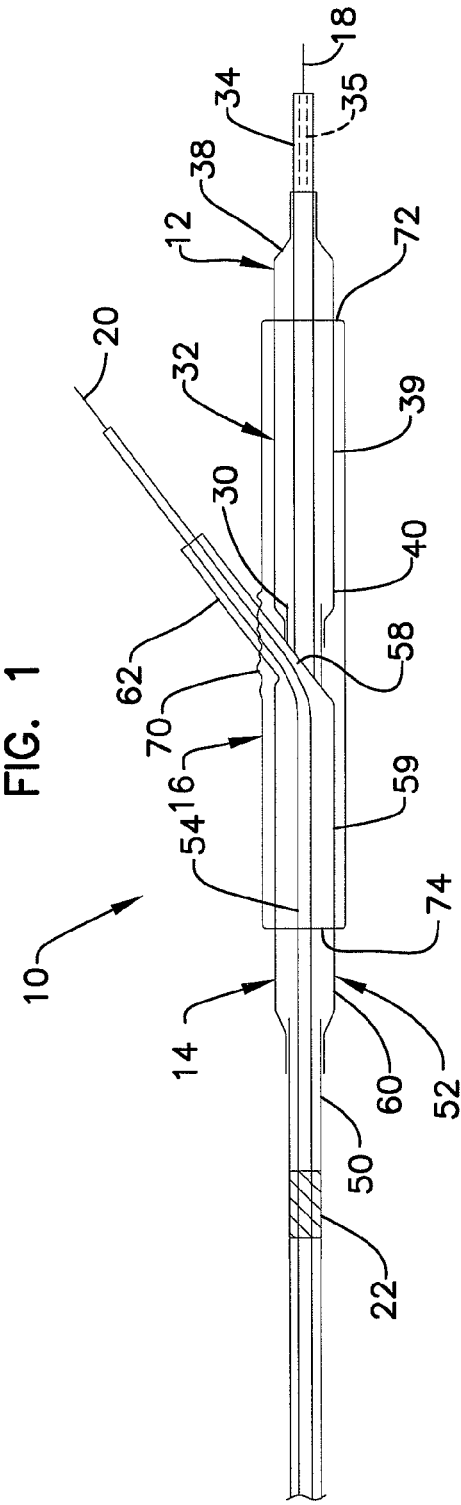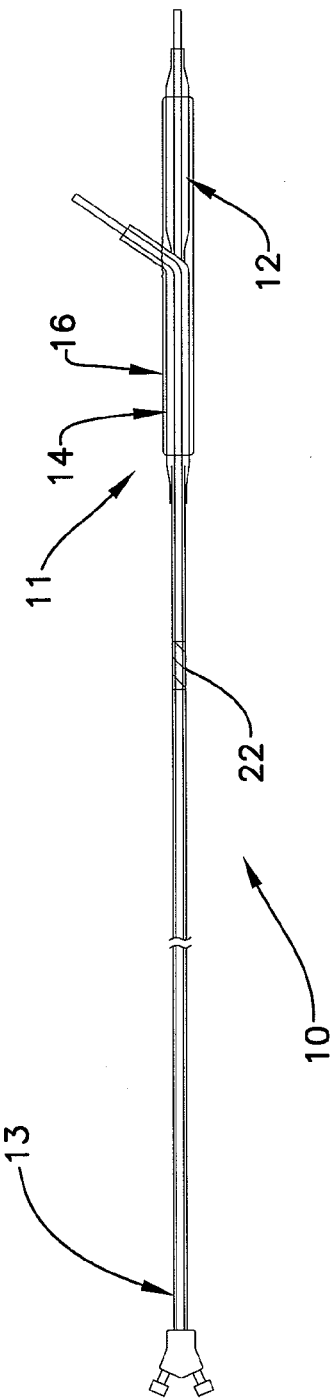

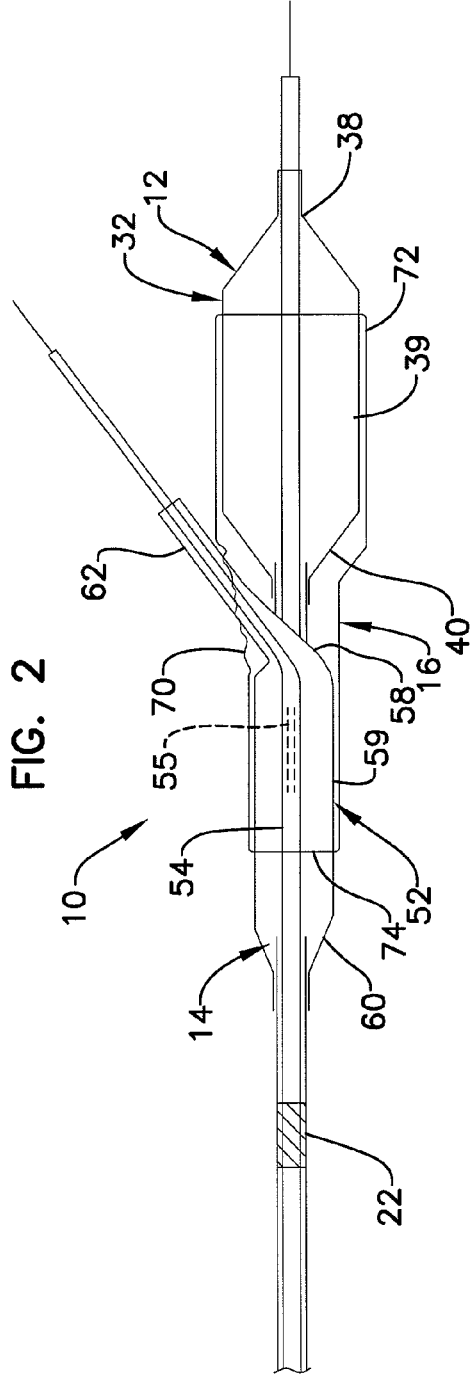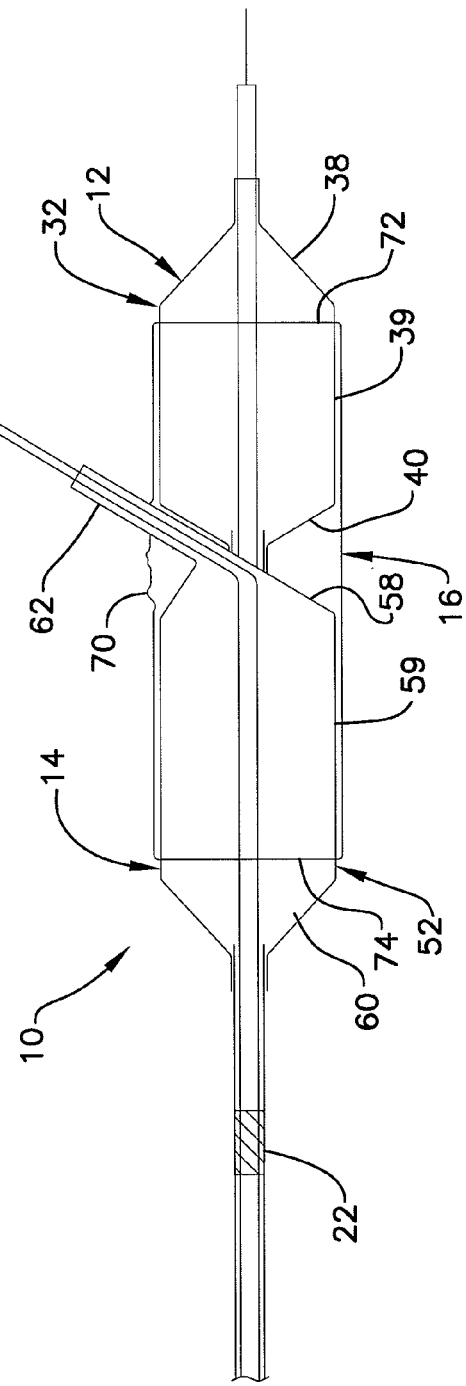

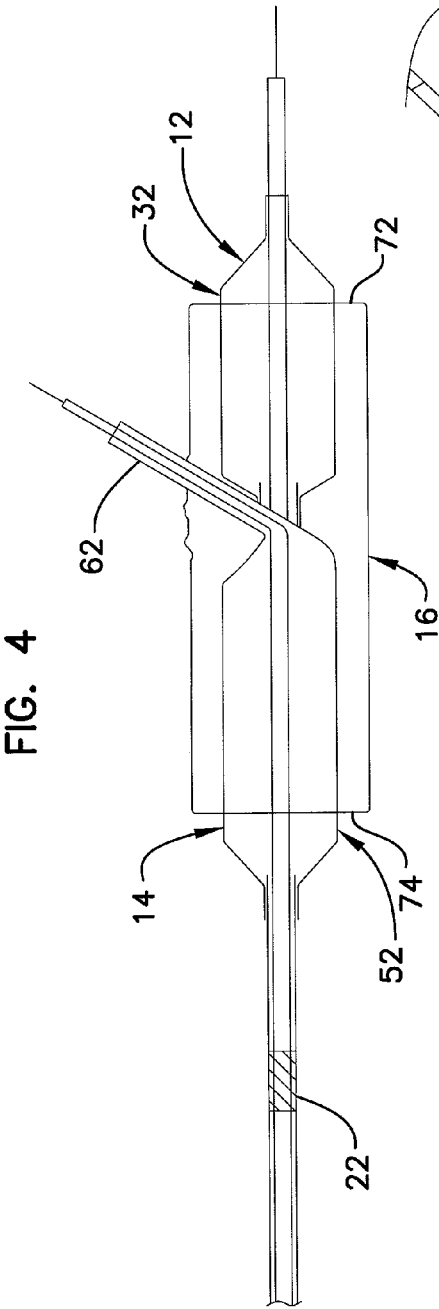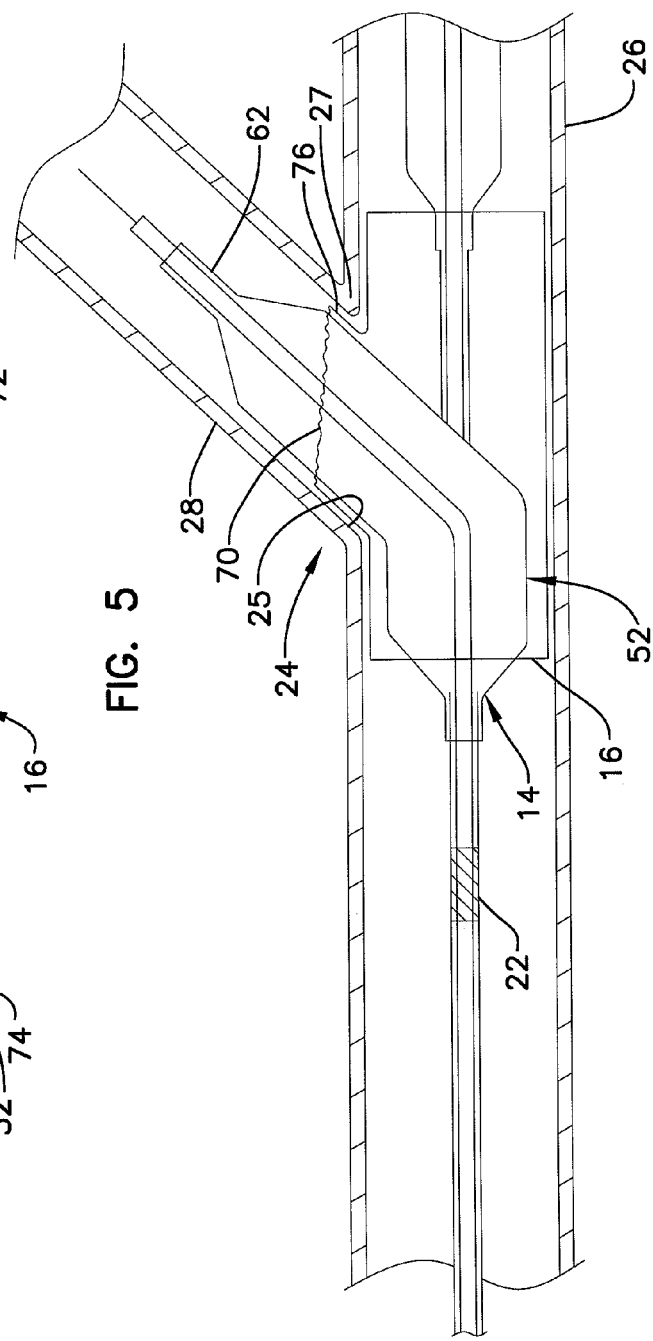

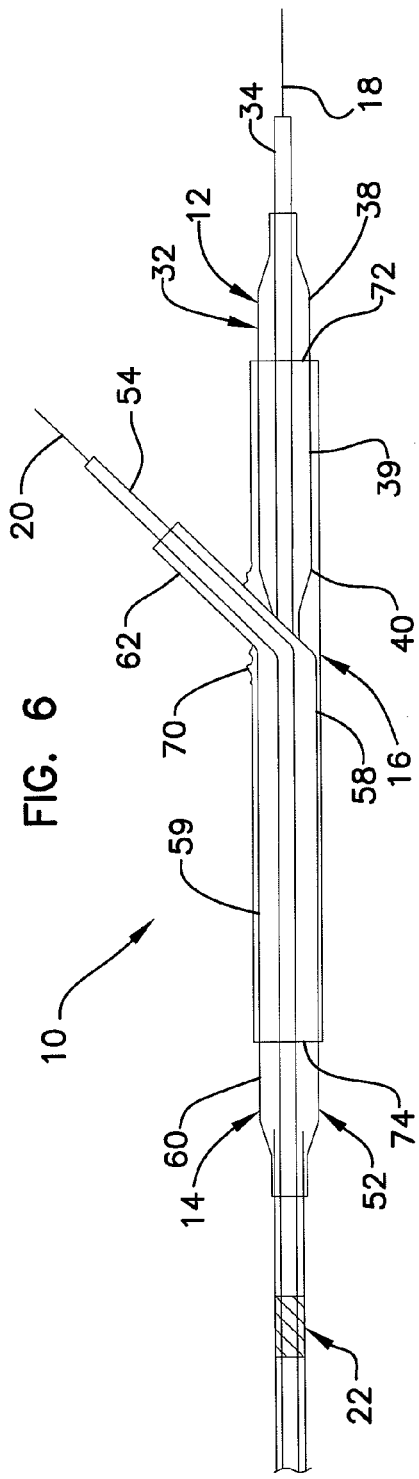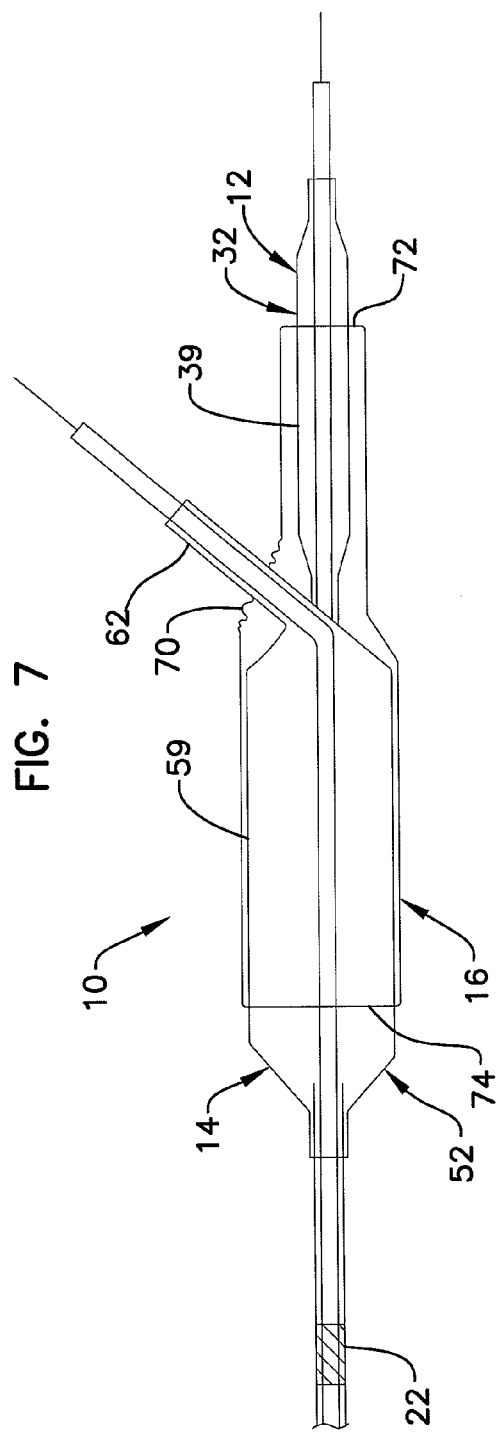

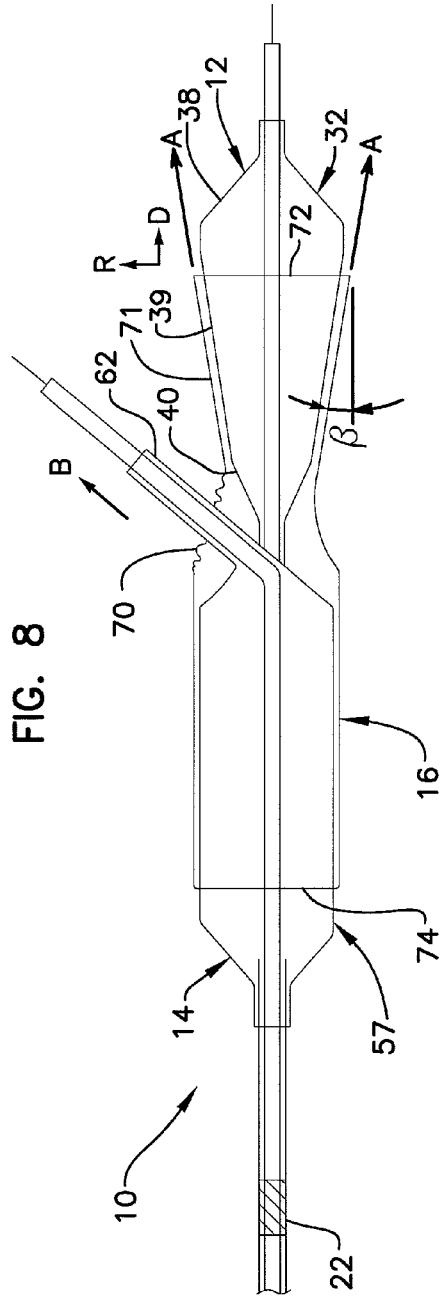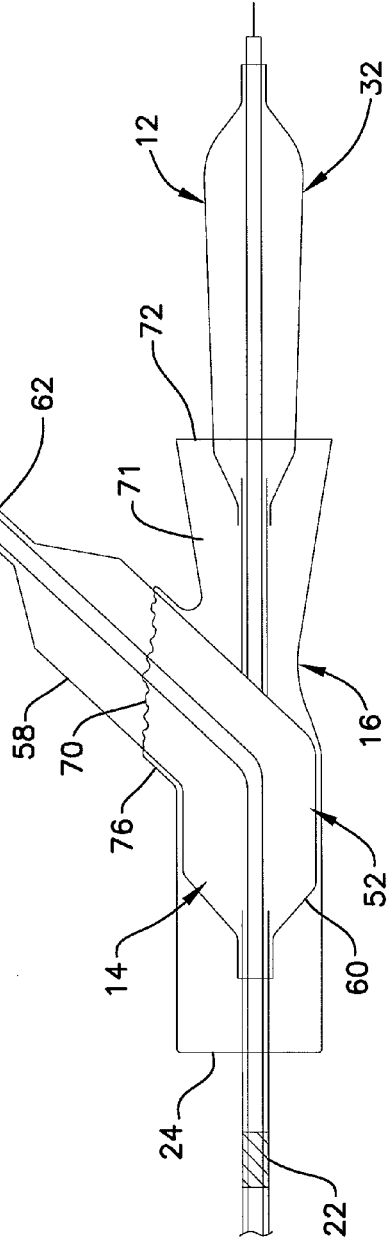

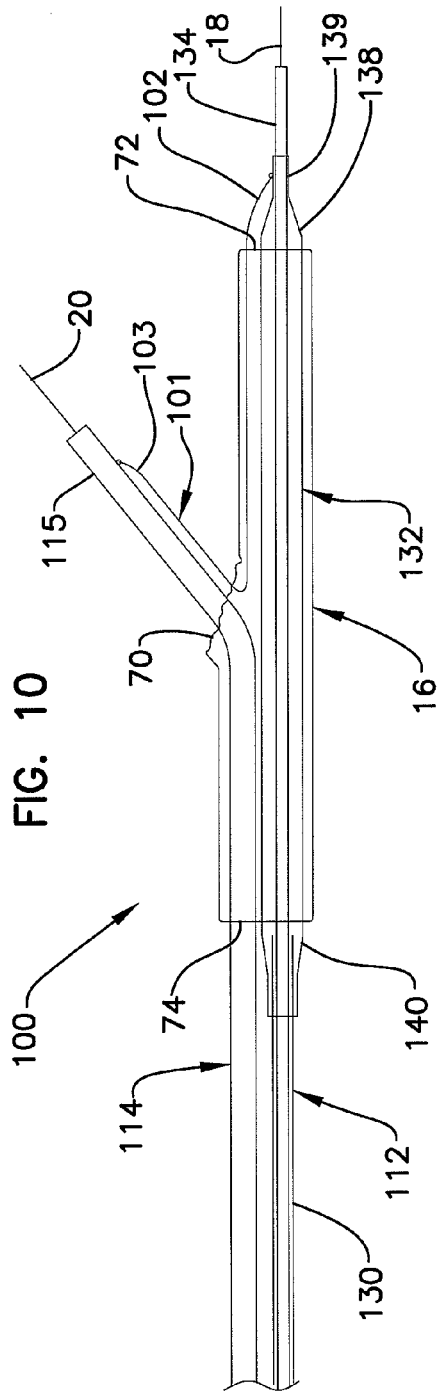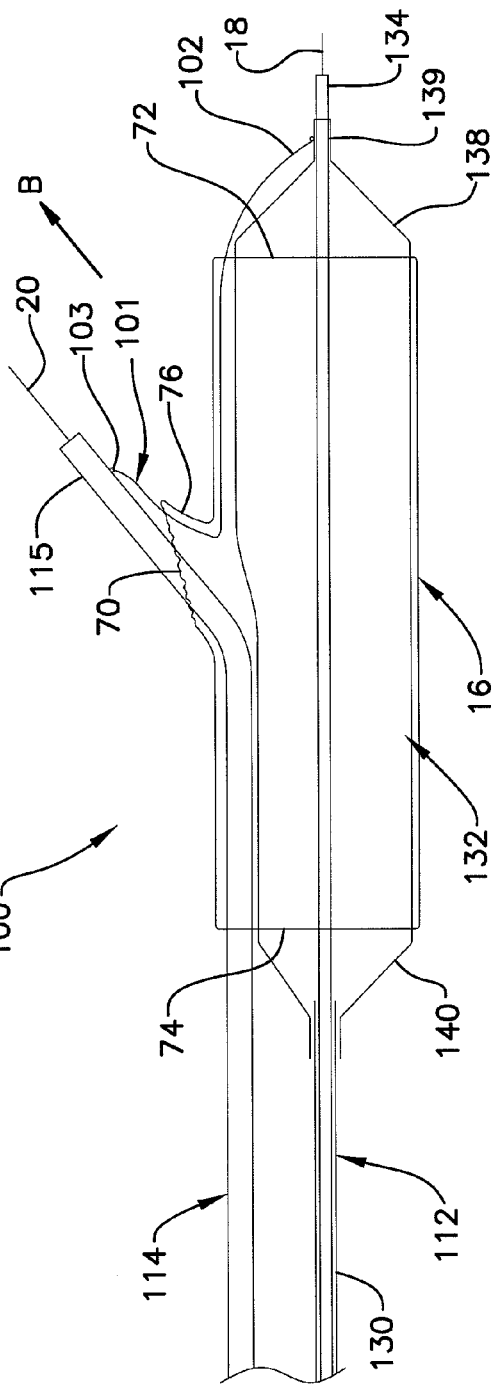

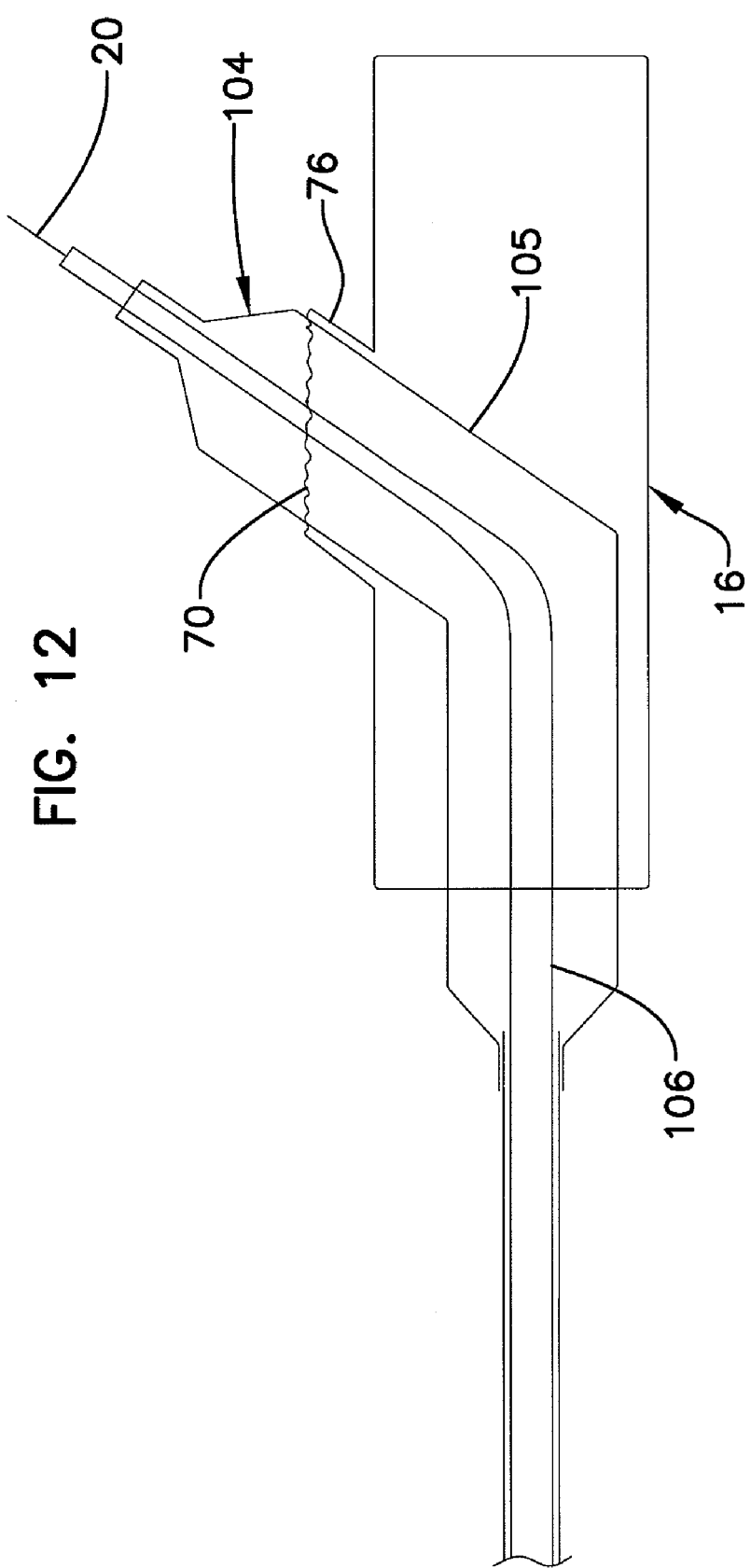

STAGGERED TWO BALLOON BIFURCATION CATHETER ASSEMBLY AND METHODS

TECHNICAL FIELD

This disclosure relates to catheter assemblies configured for treatment of a vessel bifurcation. Preferred arrangements provide for dual balloon catheter assemblies wherein the balloons are staggered axially relative to each other.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed. One challenge related to treatment of a vessel bifurcation involves treating with a stent the area of the vessel bifurcation surrounding the ostium into a branch vessel. Another challenge relates to minimizing the outer profile of the catheter assembly used to treat the vessel bifurcation for purposes of improving the ease of advancing the catheter assembly to the vessel bifurcation.

SUMMARY OF THE DISCLOSURE

The present disclosure relates to stent delivery systems that include a catheter assembly having first and second balloon members. The stent includes a distal open end, a proximal open end, a side branch aperture, and an expandable structure defining the side branch aperture. The side branch aperture is defined in a sidewall of the stent at a location between the proximal and distal open ends. The expandable structure is configured to move into a radial outward orientation relative to the sidewall of the stent. Portions of the first and second balloon members are positioned within the stent with the first balloon member extending distally from the distal open end of the stent and the second balloon member extending proximally from the proximal open end of the stent. The first and second inflatable members can be arranged generally coaxially within the stent. The expandable structure of the stent is moved into the radial outward orientation by advancing a portion of the second balloon member through the side branch aperture. In some arrangements, the second balloon member is at least partially inflated when advanced through the side branch aperture.

The first and second balloon members can be mounted to first and second catheter branches, respectively. A portion of the second catheter branch can be positioned extending through the side branch aperture prior to advancing the second balloon member through the side branch aperture. Various inflation sequences can be used to anchor the stent relative to the vessel prior to advancing the second balloon member through the side branch aperture. In some arrangements, the inflation sequence itself can be used to help advance the proximal inflation member through the side branch aperture.

In other arrangements, structures secured between first and second catheter branches of a catheter assembly can be used to move the expandable structure into the radial outward orientation upon inflation of a balloon member of the catheter assembly.

There is no requirement that an arrangement include all features characterized herein to obtain some advantage according to this disclosure.

BRIEF DESCRIPTION OF THE DRAWINGS

FIG. 1 is a schematic side view of a distal end portion of a stent delivery system constructed according to principles of this disclosure with first and second balloon members in a deflated state.

FIG. 1A is a schematic side view of the stent delivery system shown in FIG. 1 including a proximal end portion thereof.

FIG. 2 is a schematic side view of the stent delivery system of FIG. 1 with the first balloon member at least partially inflated.

FIG. 3 is a schematic side view of the stent delivery system of FIG. 1 with the first and second balloon members at least partially inflated.

FIG. 4 is a schematic side view of the stent delivery system of FIG. 1 with the first and second balloon members partially deflated.

FIG. 5 is a schematic side view of the stent delivery system of FIG. 1 with the first and second balloon members advanced distally and positioned relative to a vessel bifurcation.

FIG. 6 is a schematic side view of another stent delivery system constructed according to principles of this disclosure with the first and second balloon members in a deflated state.

FIG. 7 is a schematic side view of the stent delivery system shown in FIG. 6 with the second balloon member in an inflated state.

FIG. 8 is a schematic side view of the stent delivery system shown in FIG. 6 with the second balloon member in an at least partially inflated state and the first balloon member in an at least partially inflated state.

FIG. 9 is a schematic side view of the stent delivery system shown in FIG. 8 with the first and second balloon members advanced distally.

FIG. 10 is a schematic side view of another stent delivery system constructed according to principles of this disclosure, the stent delivery system including a tether member and a balloon member in a deflated state.

FIG. 11 is a schematic side view of the stent delivery system shown in FIG. 10 with the second balloon member in an at least partially inflated state.

FIG. 12 is a schematic side view of the stent delivery system shown in FIG. 6 with the second balloon member in an at least partially inflated state.

DETAILED DESCRIPTION

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The example catheter assemblies disclosed herein include first and second catheter branches. Although alternatives are possible, each of the catheter branches generally include a guidewire housing and an inflatable balloon member. A distal end portion of second catheter branch is configured to extend into a branch vessel at a vessel bifurcation while a distal end portion of the first catheter branch is positioned in a main vessel at the vessel bifurcation. The catheter assembly is configured to deliver a stent to the vessel bifurcation and expand the stent into engagement with the vessel. The second catheter branch can be used to help align features of the stent with an ostium (also referred to as a branch vessel opening) into the branch vessel.

The first and second catheter branches are typically coupled together at a location proximal of the balloon members. Coupling the distal and proximal catheter branches together permits concurrent axial movement of the distal and proximal catheter branches. For example, if one of the first and second catheter branches is advanced distally, the other of the catheter branches is also advanced distally.

One aspect of the present disclosure relates to opening of a side branch aperture of the stent using the second catheter branch. The side branch aperture is defined by stent structure that is expandable into a radially outward orientation relative to a sidewall of the stent. By advancing the second catheter branch at least partially distally through the side branch aperture, the expandable stent structure that defines the side branch aperture is moved toward the radially outward orientation. In some arrangements, at least partially inflating the balloon of the second catheter branch prior to advancing the second catheter branch can help move the expandable stent structure into the radially outward orientation. Further inflation of the balloon of the second catheter branch while the balloon is positioned extending through the side branch aperture can further expand the expandable stent structure towards the radial outward orientation and into engagement with the branch vessel of the vessel bifurcation.

Another aspect of the present disclosure relates to distally advancing the proximal catheter branch using forces resulting from a sequence of inflating the balloon members of the first and second catheter branches. The first and second catheter branches are secured together at a location proximal of the balloon members of the first and second catheter branches. Prior to the inflation sequence, a portion of the balloon member of the second catheter branch is positioned within the stent with a distal end portion of second catheter branch extending through the side branch aperture. Further, a portion of the balloon member of the first catheter branch is positioned within the stent at a location distal of the balloon member of the second catheter branch, and a distal end portion of the first catheter branch balloon extending distal of the distal open end of the stent. The side branch aperture of the stent is aligned with an ostium of the branch vessel. The inflation sequence is initiated by at least partially inflating the balloon member of the second catheter branch to expand a proximal portion of the stent into engagement with the main vessel of the vessel bifurcation. The at least partially inflated balloon of the second catheter branch is then partially deflated. The balloon member of the first catheter branch is then inflated. A force having axial components directed in the distal direction is generated as the balloon member of the first catheter branch is inflated due to the resulting shape of the distal end portion of the stent that is formed as the balloon member of the first catheter branch is inflated. This axially directed force advances the first and second catheter branches distally, thereby advancing the balloon of the second catheter branch through the side branch aperture to move the expandable stent structure towards the radially outward orientation. Further inflation of the balloon of the second catheter branch can provide further movement of the expandable stent structure into the radially outward orientation and into engagement with the branch vessel of the vessel bifurcation.

A further aspect of the present disclosure relates to the use of a tether member to expand the expandable stent structure towards the radially outward orientation. While alternatives are possible, the catheter assembly can include a main catheter branch and a secondary catheter. The main catheter branch includes a main balloon member and a main guidewire housing member, wherein the main guidewire housing member is sized to advance over a main guidewire. The secondary catheter defines a branch guidewire housing member sized to advance over a branch guidewire. The main balloon extends through the stent from the proximal open end to the distal open end of the stent. The secondary catheter extends into the proximal open end of the stent and out through the side branch aperture of the stent. The tether member has a proximal end portion and a distal end portion. The proximal end portion of the tether member is secured to the secondary catheter at a location distal of the side branch aperture. The distal end portion of the tether member is secured to the main catheter branch at a location distal of the main balloon. In one example, the tether member is secured to the main catheter branch at a connection point of a distal waist of the main balloon to the main guidewire housing. When the main balloon member is inflated, the main balloon member applies a tension force to the tether member. The applied tension force results in the tether member exerting a force upon the expandable structure of the stent that moves at least a portion of the expandable structure into the radially outward orientation. The catheter assembly can be retracted proximally from the stent, followed by advancing a post dilation balloon catheter through the side branch aperture. Inflation of the post dilation balloon further moves the expandable stent structure toward the radially outward orientation and into engagement with the branch vessel of the vessel bifurcation.

As used herein, the term "at least partially inflated" as it related to a balloon member is defined as an amount of inflation that is greater than a fully deflated balloon that is folded and prepared for insertion into a patient for treatment of the patient. In some cases, "at least partially inflated" includes a level of inflation that causes the balloon member to become unfolded. In other cases, "at least partially inflated" includes addition of any amount of inflation fluid to the balloon member. The term "at least partially inflated" can also be defined as an amount of inflation significant enough to at least partially expand a stent that has been crimped on the balloon member.

As used herein, the term "advanced at least partially distally" as it related to movement of a catheter branch or balloon member of the catheter assemblies and stent delivery systems described herein is defined a movement in a direction that has a distal direction component. A distal direction component can be defined as a distal direction, typically relative to a direction along a central axis of the structure.

The term "positioned on" as used herein is defined as being placed or mounted in relationship to another object. A first object positioned on a second object can be secured or connected together. Further, a first object positioned on a second object can extend around the second object fully or partially. The Example Catheter Assembly and Methods of FIGS. 1-5

Referring to FIGS. 1-5, an example catheter assembly 10 is shown and described. The catheter assembly 10 includes a distal catheter branch 12 (also referred to herein as a first catheter branch) and a proximal catheter branch 14 (also referred to herein as a second catheter branch). A stent 16 is positioned on or otherwise extending around at least a portion of each of the distal and proximal branches 12, 14. The distal catheter branch 12 is configured to advance over a main vessel guidewire 18. The proximal catheter branch 14 is configured to advance over a branch vessel guidewire 20. The distal and proximal catheter branches 12, 14 intersect at a proximal joint 22. The distal and proximal catheter branches 12, 14 can be connected together at the proximal joint 22. The catheter assembly 10 is used to treat a vessel bifurcation 24 (see FIG. 5) that includes a main vessel 26 and a branch vessel 28. The distal and proximal catheter branches 12, 14 are located at a distal end portion 11 of the catheter assembly 10 opposite a proximal end portion 13 of the catheter assembly 10 (see FIG. 1A).

The distal catheter branch 12 includes a distal catheter shaft 30, a distal balloon 32, and a distal guidewire housing 34. The distal balloon 32 (also referred to herein as a first balloon member) includes a distal end portion 38, a proximal end portion 40, and an inflatable portion 39. The distal guidewire housing 34 defines a distal guidewire lumen 35 (see FIG. 1) and is also referred to herein as a main guidewire housing 34. The distal guidewire lumen is sized to advance over the main vessel guidewire 18.

The proximal catheter branch 14 includes a proximal catheter shaft 50, a proximal balloon 52, and a proximal guidewire housing 54. The proximal balloon 52 (also referred to herein as a second balloon member) includes a distal end portion 58, a proximal end portion 60, and an inflatable portion 59. The distal end portion 58 can include a distal balloon waist 62. The proximal guidewire housing 54 defines a proximal guidewire lumen 55 (see FIG. 2) sized to advance over the branch vessel guidewire 20. The proximal guidewire housing 54 is also referenced herein as a branch guidewire housing 54.

The proximal catheter shaft 50 is illustrated in the attached Figures positioned in view with the distal catheter shaft 30 positioned on a back side of the proximal catheter shaft 50 out of view. In other arrangements the shafts 50, 30 can be arranged differently including, for example, being stacked one on top of each other within the stent 16 with the proximal catheter shaft 50 being positioned toward the side branch aperture 70 and the distal catheter shaft 30 positioned away from the side branch aperture 70.

Although alternatives are possible, the proximal and distal balloons 32, 52 are arranged generally coaxially with each other. The proximal and distal balloons 32, 52 can also be described as being arranged in series with each other with the distal balloon 32 being positioned distal of the proximal balloon 52.

The stent 16 includes a side branch aperture 70, a stent distal open end 72, a stent proximal open end 74, and expandable structure 76 surrounding and defining the side branch aperture 70. The expandable structure 76 is shown in an expanded state in a radially outward orientation relative to a sidewall of the stent in at least FIG. 5.

The distal balloon waist 62 of the proximal catheter branch 14 can be elongated axially such that at least a portion of the distal balloon waist 62 extends through the side branch aperture 70 while the inflatable portion 59 of the proximal balloon 52 is positioned within the stent 16 at a location proximal of the side branch aperture 70. While alternatives are possible, the distal balloon waist 62 can have a length sufficient to remain extending through the side branch aperture 70 before and during inflation of either or both of the distal balloon 32 and proximal balloon 52 in any sequence of inflating the balloons 32, 52.

One aspect of using the catheter assembly 10 for treatment of a vessel bifurcation is providing the expandable structure 76 of the stent 16 extended in the radially outward orientation through an opening (i.e. an ostium) into the branch vessel 28. The expandable structure 76, when expanded in the radially outward orientation, is intended to extend from the main vessel 26 into the branch vessel 28. Further treatment of the vessel bifurcation can include positioning a post dilatation balloon in the branch vessel to further expand the expandable structure 76 into engagement with the branch vessel 28. Alternatively, a secondary stent can be positioned in the branch vessel 28 with a portion thereof overlapping the expandable structure 76.

Referring now to FIGS. 1-5, a method of delivering and deploying the stent 16 relative to the vessel bifurcation 24 is described. Typically, the main vessel guidewire 18 is advanced to the vessel bifurcation 24 to a position in which a distal end of the main vessel guidewire 18 is positioned distal of the opening 25 into the branch vessel 28. The branch vessel guidewire 20 is likewise advanced to the vessel bifurcation 24 and into the branch vessel 28. The sequence of advancing the main and branch vessel guidewires 18, 20 can vary including advancement of the guidewires 18, 20 concurrently.

Proximal ends of the main and branch vessel guidewires 18, 20 are inserted into the distal and proximal guidewire housings 34, 54, respectively. The catheter assembly 10 is advanced over the main and branch vessel guidewires 18, 20 into a position adjacent to the vessel bifurcation 24. At least a portion of the distal guidewire housing 34 is positioned within the branch vessel 28. Portions of the distal balloon waist 62 of the proximal catheter branch 14 can also be positioned within the branch vessel 28. Because the proximal guidewire housing 54 extends through the side branch aperture 70, advancing the proximal guidewire housing 54 into the branch vessel 28 helps to align the side branch aperture 70 with the ostium 25 of the branch vessel 28.

After the stent 16 has been oriented both axially and radially relative to the ostium into the branch vessel 28 (the orientation shown in FIG. 1), the distal balloon 32 is at least partially inflated to at least partially expand the stent 16, as shown in FIG. 2. In some instances, the distal balloon 32 can be fully inflated to expand that portion of the stent 16 engaged by the distal balloon 32 into a fully expanded state. In other instances, the stent 16 is only partially expanded in that area engaged by the at least partially inflated distal balloon 32. Typically, that portion of the stent 16 being engaged by the distal balloon 32 is expanded sufficiently to engage the main vessel 26 to anchor the stent 16 in a fixed axial and radial position relative to the vessel bifurcation 24.

Referring now to FIG. 3, the proximal balloon 52 is at least partially inflated to at least partially expand that portion of the stent 16 that is engaged by the proximal balloon 52. In some instances, the at least partially inflated distal balloon 32 can be at least partially deflated prior to inflation of the proximal balloon 52. In other instances, such as shown in FIG. 3, both of the proximal and distal balloons 52, 32 are in an at least partially inflated state at the same point in time.

As described above with reference to the distal balloon 32, the proximal balloon 52 can be inflated to various inflated states ranging from only partially inflated to fully inflated. When partially inflated, that portion of the stent 16 engaged by the proximal balloon 52 is typically only partially expanded, whereas when the proximal balloon 52 is fully inflated, that portion of the stent 16 engaged by the proximal balloon 52 is typically fully expanded and anchored in engagement with the main vessel 26 at a location proximal of the ostium 25 of the branch vessel 28.

Inflation of the distal and proximal balloons 32, 52 can occur in sequential steps. For example, the distal balloon 32 can be partially inflated, followed by partial inflation of the proximal balloon 52, followed by further inflation of the distal balloon 32, followed by further inflation of the proximal balloon, and so forth. In other instances, the distal and proximal balloons 32, 52 can be inflated simultaneously. In yet further instances, as described below with reference to FIGS. 6-9, the proximal balloon 32 can be at least partially inflated first followed by at least partial inflation of the distal balloon 32. The order of inflating the distal and proximal balloons 32, 52 as well as the amount of inflation in each step of inflation can influence how the stent 16 is expanded as well as axial movement of one or both of the distal and proximal catheter branches 12, 14 relative to the stent 16 and the vessel bifurcation 24.

Referring now to FIG. 4, the distal and proximal balloons 32, 52 are at least partially deflated from the more inflated states shown in FIG. 3 and the stent 16 retains its expanded state from the more inflated balloon states shown in FIG. 3. The distal and proximal balloons 32, 52 can be deflated different amounts as desired, such as being fully deflated (i.e. an attempt has been made to draw all inflation fluid from the balloon). In some arrangements, one or both of the distal and proximal balloons 32, 52 can remain in a fully inflated state during the subsequent step of advancing the catheter assembly 10 in at least partially distally.

In the present arrangement, at least a portion of the distal balloon waist 62 extends through the side branch aperture 70 prior to distal advancement of the proximal catheter branch 14. This arrangement can provide for improved ease in distal advancement of the proximal catheter branch 14 through the side branch aperture 70 to move the expandable structure 76 into the radially outward orientation shown in FIG. 5. The amount of movement of the expandable structure 76 can be controlled in part by the extent of inflation of the proximal balloon 52. Expansion of the expandable structure 76 can also be limited by the size of the ostium 25 into the branch vessel 28, which opening is at times further restricted by the buildup of plaque or other deposits within the vessel bifurcation 24.

With the proximal balloon 52 positioned within the side branch aperture 70 as shown in FIG. 5, the proximal balloon 52 can be further inflated to further extend the expandable structure 76 in the radially outward orientation and into engagement with the branch vessel 28. Further distal advancement of the catheter assembly 10 can be commenced while the proximal balloon 52 is at least partially inflated. Typically, the catheter assembly 10 is advanced only in the distal direction while the proximal balloon 52 is in an inflated state.

After deployment of the stent 16 to treat the vessel bifurcation 24 as shown with reference to FIG. 5, the distal and proximal balloons 32, 52 are at least partially deflated and the catheter assembly 10 can be retracted proximally while leaving one or more of the main and branch vessel guidewires 18, 20 in the main and branch vessels 26, 28, respectively. Additional treatment catheters such as a post dilatation balloon catheter can be used to further expand or otherwise move portions of the stent 16 to treat the vessel bifurcation 24. In one example, a secondary stent mounted to a secondary balloon catheter (not shown) can be advanced through the side branch aperture 70 and into the branch vessel 28 for further treatment of the vessel 28.

The proximal joint 22 is positioned proximal of the stent 16. The proximal joint 22 is typically positioned within about 0.5 cm to about 10 cm of the proximal end 60 of the proximal balloon 52, and more preferably within about 1 to about 3 cm of the proximal end 60 of the proximal balloon 52. The distal and proximal catheter branches 12, 14 can be formed integral with each other. Alternatively, the distal and proximal catheter branches 12, 14 can be secured together at the proximal joint 22 with, for example, an adhesive, heat bonding, or laser bonding. Inclusion of a proximal joint 22 in the catheter assembly 10 provides for concurrent axial movement of both of the distal and proximal catheter branches 12, 14 when an axially force is applied to one or the other of the distal and proximal catheter branches 12, 14.

The orientation of the distal and proximal branches 12, 14 shown in FIGS. 1-4 can be referred to as a retracted orientation relative to the stent 16. The orientation of at least the proximal branch 14 relative to the stent 16 shown in FIG. 5 can be referred to as an advanced orientation. The term "advanced orientation" is defined as an orientation wherein movement had occurred to advance the catheter branch relative to the stent. In the context of the present disclosure, the term "advanced orientation" refers to at least partially distally advancing the proximal catheter branch 14 relative to the stent 16, and particularly relative to the side branch aperture 70 of the stent 16.

The Example Methods of FIGS. 6-9

FIG. 6 illustrates catheter assembly 10 with the distal and proximal balloons 32, 52 in a deflated state. The distal and proximal catheter branches 12, 14 are advanced over main and branch vessel guidewires 18, 20, respectively, to a vessel bifurcation treatment site wherein the main and branch vessel guidewires 18, 20 are positioned within main and branch vessels 26, 28, respectively. The proximal guidewire housing 54 extends out of the side branch aperture 70 of the stent 16 and into the branch vessel 26. In some arrangements, at least a portion of the distal balloon waist 62 also extends through the side branch aperture 70 prior to inflation of the distal and proximal balloons 32, 52. The proximal guidewire housing 54 can help axially and radially align the side branch aperture 70 with the ostium 25 of the branch vessel 26.

Referring now to FIG. 7, the proximal balloon 52 is at least partially inflated to at least partially expand that portion of the stent 16 being engaged by the proximal balloon 52. Typically, the proximal balloon 52 expands the stent 16 sufficiently to engage at least a portion of the stent 16 with the vessel walls of the vessel bifurcation to anchor the stent 16 relative to the vessel bifurcation 24.

After the proximal balloon 52 is at least partially inflated, the distal balloon 32 is then at least partially inflated as shown in FIG. 8. The stent 16 first begins to expand where there is least resistance to expansion, which is typically adjacent the distal open end 72, and expand last where resistance to expansion is greatest, which is typically at a location along the stent between the branch aperture 70 and the distal open end 72. The result of these variations in expansion along the stent length, the stent begins to take on a tapered shape having an angled stent portion 71. The angled stent portion 71 is arranged in angle β (see FIG. 8) relative to a longitudinal axis passing through the distal guidewire housing 34.

The shape of the angled stent portion 71 in combination with further inflation of the distal balloon 32 creates a force component applied to the distal balloon 32 in the axial direction A (see FIG. 8) as the distal balloon 32 further inflates. This force component in the direction A has a distal component D and a radial component R that results in distal advancement of the catheter assembly 10 into the orientation shown in FIG. 9.

Advancement of the catheter assembly 10 and the distal direction while portions of the distal balloon waist 62 and proximal guidewire housing 54 are extending through the side branch aperture 70 results in the proximal catheter branch 14 moving distally through the side branch aperture 70. This distal advancement of the proximal catheter branch 14 provides engagement with the expandable structure 76 to move the expandable structure 76 toward the radially outward orientation. The expandable structure 76 can be further expanded and the side branch aperture 70 further opened by maintaining the proximal balloon 52 at least partially inflated prior to distal advancement of the proximal catheter branch 14, and further inflation of the proximal balloon 52 after the distal advancement. Further advancement of the catheter assembly 10 while the proximal balloon 52 is inflated can also promote further movement of expandable structure 76 towards the radially outward orientation and into engagement with the branch vessel.

"Watermelon seeding" is a term used to describe the movement that occurs by a portion of the catheter assembly when the stent is positioned over only one tapered/conical end of an inflation balloon. The unrestricted portion of the balloon (tapered/conical end of the balloon without stent coverage) opens first when the balloon begins to inflate. The partially inflated balloon takes on a shape that resembles a tapered/conical shape from one end of the balloon to the other end, wherein the smaller end of the balloon is within the stent and the larger end of the balloon is outside the stent. The balloon counteracts the restriction caused by the stent by moving axially away from the stent as the balloon is further inflated. The resultant axial movement of the balloon relative to the sent is referred to as "watermelon seeding" because of comparisons to a similar movement that occurs when a watermelon seed is squeezed between a person's pressed lips, which subsequently shoots the seed out from the lips.

The distal and proximal balloons 32, 52 can be deflated and retracted proximally relative to the stent 16. One or both of the distal balloons 32, 52 can be further inflated while positioned within the stent 16 to expand other portions of the stent 16 such as the angled portion 71 into engagement with the vessel bifurcation. In some instances, the entire catheter assembly 10 can be retracted distally out of the patient's body while leaving one or both of the main and branch vessel guidewires 18, 20 in position within the vessels of the vessel bifurcation. Additional treatment devices such as a post dilation balloon catheter or a secondary stent carried by a secondary balloon catheter can be advanced to the vessel bifurcation treatment site and used to further expand portions of the stent 16 or treat other aspects of the vessel bifurcation.

The Example Catheter Assembly of FIGS. 10-12

Another example catheter assembly 100 is now described with reference to FIGS. 10-12. The catheter assembly 100 includes a main catheter branch 112, a side catheter branch 114 having a distal end portion 115, and a tether member 101. The tether member 101 includes a distal end 102 and a proximal end 103. A stent 16 is operably mounted to the main catheter branch 112. The main catheter branch 112 includes a catheter shaft 130 and a balloon member 132. The balloon member 132 includes distal and proximal ends 138, 140 and defines a guidewire housing 134. The stent 16 includes a side branch aperture 70, a stent distal open end 72, a stent proximal open end 74, and expandable structure 76 that defines the side branch aperture 70.

The tether member 101 is secured to both the main catheter branch 112 and the side catheter branch 114. The distal end 102 of the tether 101 is secured to the main catheter shaft 112 at a location distal of the balloon 132. In one example, the distal end 102 is secured to the main catheter branch 112 at a distal waist portion 139 of the balloon member 132. In other arrangements, the distal end 102 is secured at another location along the balloon member 132 distal of the side branch aperture 70. In yet other examples, the distal end 102 can be secured to the guidewire housing 34 at a location distal of the side branch aperture 70.

The proximal end 103 of the tether 101 is secured to the side catheter branch 114. In one arrangement, as shown in FIG. 10, the proximal end 103 is secured to the side catheter branch 114 at a location outside of the stent 16 before the stent is expanded. In other arrangements, the proximal end 103 is secured to the side catheter branch 114 at a location that is located within the stent 16 before the stent is expanded and positioned outside of the stent when the stent is at least partially expanded.

The tether member 101 can be constructed as a wire, string, thread or other structure. The tether member 101 can have various sizes (e.g., length, width and thickness dimensions) and cross-sectional shapes. In one example, the tether member 101 has a sheet-like structure having a significantly greater width than thickness dimension. In one example, the tether member 101 has a width dimension of about 1 to about 3 mm (more preferably about 2 mm), a length dimension of about 10 to about 20 mm (more preferably about 16 mm), and a thickness dimension of about 0.0005 to about 0.002 inches (more preferably about 0.001 inches) while still maintaining adequate tensile strength in the tether member 101. Tether member 101 can be constructed of many different materials such as, for example, metals, metal alloys, polymer based materials (e.g., Pebax and Teflon), and shape memory materials such as Nitinol.

Referring now to FIGS. 10-12, an example method of treating a vessel bifurcation is now described using the catheter assembly 100. The main and branch vessel guidewires 18, 20 are advanced to the vessel bifurcation (e.g., vessel bifurcation 24 shown in FIG. 5) and positioned with the main vessel guidewire 18 in the main vessel (e.g., main vessel 26 shown in FIG. 5) and the branch vessel guidewire 20 in the branch vessel (e.g., main vessel 28 shown in FIG. 5). The catheter assembly 100 is then advanced over the guidewires 18, 20 with the main catheter branch 112 being advanced over the main vessel guidewire 18 and the side catheter branch 114 being advanced over the branch vessel guidewire 20. The catheter assembly 100 is advanced distally until the distal end portion 115 and the side catheter branch 114 is positioned within the branch vessel at the vessel bifurcation. The catheter assembly 100 is adjusted axially and distally until the side branch aperture 70 is oriented relative to the ostium into the branch vessel.

Referring now to FIG. 11, the balloon 132 is inflated, thereby expanding the stent 16 into engagement with the main vessel of the vessel bifurcation. Inflating the balloon 32 creates tension in the tether 101 thereby causing application of a force in the direction B upon the expandable structure 76 of the stent 16. The force applied by the tether 101 in a direction B causes movement of the expandable structure 76 in a radially outward orientation such as into the orientation shown in FIG. 11. After the expandable structure 76 has been at least partially moved in the radially outward orientation, the balloon 132 is deflated and to ensure adequate placement of the expandable structure in the radially outward orientation the entire catheter can be pushed in the distal direction to further expand the structure in the radial direction. Once suitable expansion is achieved, the main and side catheter branches 112, 114 are retracted proximally out of the patient.

In a further treatment step, a secondary catheter 104 is advanced over the branch vessel guidewire 20, through the side branch aperture 70, and into the branch vessel. The secondary catheter 104 includes a balloon 105 and a guidewire housing 106. The branch vessel guidewire 20 extends through the guidewire lumen 106. The balloon 105 is inflated to further expand the expandable structure 76. This further expansion of the expandable structure 76 can help ensure that the expandable structure 76 engages a carina of the vessel bifurcation and other portions of the branch vessel. The balloon 105 can then be deflated and retracted proximally from the patient. In a still further step (not shown) another secondary catheter that carries a branch stent can be advanced over the branch vessel guidewire 20 and through the side branch aperture 70 into the branch vessel where the branch stent is deployed to further treat the branch vessel.

Materials and Other Considerations

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various copolymers and blends of polyethylene, ionomers, polyesters, polycarbonates, polyamides, poly-vinyl chloride, acrylonitrile-butadiene-styrene copolymers, polyether-polyester copolymers, and polyether-polyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 1F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in, for example, in U.S. Pat. Nos. 6,210,429 and 6,325,826 to Vardi et al., and co-pending U.S. patent application Ser. No. 10/644,550, filed on Aug. 21, 2003, and titled "Stent With a Protruding Branch Portion For Bifurcated Vessels," the entire contents of which are incorporated herein by reference.

In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radially outward orientation relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

Conclusion

One aspect of the present disclosure relates to a stent delivery system that includes a stent, a first catheter branch and a second catheter branch. The stent defines an interior volume and includes a distal open end, a proximal open end, and expandable structure defining a side branch aperture. The expandable structure is configured to move into a radial outward orientation. The first catheter branch includes a distal end portion, a proximal end portion, and a first balloon. The first balloon is positioned on the first catheter branch and includes a distal end portion and a proximal end portion. The proximal end portion of the first balloon is positioned within the interior volume of the stent and the distal end portion of the first balloon is positioned distal of the distal open end of the stent. The second catheter branch includes a distal end portion, a proximal end portion, and a second balloon. The second balloon is positioned on the second catheter branch and includes a distal end portion, a proximal end portion, and an inflatable portion. The second balloon being movable between a retracted orientation wherein the inflatable portion is positioned proximal of the side branch aperture of the stent and the distal end portion of the second catheter branch extends through the side branch aperture, and an advanced orientation wherein the second balloon is advanced at least partially distally through the side branch aperture. In some arrangements, the second balloon is at least partially inflated before being moved from the retracted orientation to the advanced orientation.

Another aspect of the present disclosure relates to a stent delivery system adapted for use with a stent. The stent has a distal open end, a proximal open end, a side branch aperture, and expandable structure defining the side branch aperture. The expandable structure is configured to move into a radial outward orientation relative to the stent. The stent delivery system includes a first balloon and a second balloon. The first balloon has a distal end portion and a proximal end portion. The distal end portion extends distally of the distal open end of the stent, and the proximal end portion is positioned within the stent. The second balloon includes a distal end portion, a proximal end portion, and an inflatable portion. The second balloon is configured to move between a retracted orientation wherein the inflatable portion is positioned proximal of the side branch aperture of the stent, and an advanced orientation wherein the second balloon is advanced at least partially distally through the side branch aperture. The second balloon can be at least partially inflated before being moved from the retracted orientation to the advanced orientation.

A further aspect of the present disclosure relates to a method of expanding a stent with a catheter assembly. The catheter assembly includes a first balloon and a second balloon that each include a distal end portion, a proximal end portion, and an inflatable portion. The stent includes a distal open end, a proximal open end, and expandable structure that defines a side branch aperture in the stent. The expandable structure is movable into a radial outward orientation. The method steps include positioning the first balloon in a first orientation with the distal end portion of the first balloon extending distally of the distal open end of the stent and the proximal end portion of the first balloon positioned within the stent, and positioning the second balloon in a retracted orientation with the proximal end portion of the second balloon extending proximal of the proximal open end of the stent and the inflatable portion of the second balloon positioned proximal of the side branch aperture. The method also includes at least partially inflating the second balloon, and advancing the at least partially inflated second balloon at least partially distally into an advanced orientation wherein at least a portion of the inflatable portion of the second balloon extends through the side branch aperture of the stent to move the expandable structure towards the radial outward orientation.

The above specification, examples and data provide a complete description of the manufacture and use of the composition of the invention. Since many aspects of the invention can be made without departing from the spirit and scope of the invention, the invention resides in the claims hereinafter appended.

We claim:

1. A stent delivery system, comprising:
   (a) a stent, the stent defining an interior volume and having a distal open end, a proximal open end, and expandable structure defining a side branch aperture, the expandable structure being configured to move into a radial outward orientation;
   (b) a first catheter branch including:
      i. a distal end portion and a proximal end portion; and
      ii. a first balloon positioned on the first catheter branch, the first balloon having a distal end portion and a proximal end portion, the proximal end portion of the first balloon being positioned within the interior volume of the stent and the distal end portion of the first balloon being positioned distal of the distal open end of the stent; and
   (c) a second catheter branch including:
      i. a distal end portion and a proximal end portion; and
      ii. a second balloon positioned on the second catheter branch, the second balloon including a distal end portion including a distal waist portion, a proximal end portion, and an inflatable portion positioned proximal of the proximal end portion of the first balloon, the second balloon being movable between:
         (1) a retracted orientation wherein the inflatable portion is positioned proximal of the side branch aperture of the stent and the distal end portion of the second catheter branch extends through the side branch aperture; and
         (2) an advanced orientation wherein the second balloon is advanced at least partially distally through the side branch aperture, wherein the distal waist portion extends through the side branch aperture prior to and during movement of the second balloon from the retracted orientation to the advanced orientation.

2. The stent delivery system of claim 1, wherein the second catheter branch intersects the first catheter branch at a proximal joint, the proximal joint being located proximal of the proximal end portion of the first balloon and proximal of the proximal end portion of the second balloon.

3. The stent delivery system of claim 2, wherein the proximal joint is located distal of the proximal end portions of each of the first and second catheter branches.

4. The stent delivery system of claim 1, wherein the second balloon is at least partially inflated before being moved from the retracted orientation to the advanced orientation.

5. The stent delivery system of claim 1, wherein the inflatable portion of the second balloon engages the expandable structure when in the advanced orientation to at least partially move the expandable structure into the radial outward orientation.

6. A stent delivery system adapted for use with a stent, the stent having a distal open end, a proximal open end, a side branch aperture, and expandable structure defining the side branch aperture, the expandable structure being configured to move into a radial outward orientation relative to the stent, the stent delivery system comprising:
(a) a first balloon having a distal end portion and a proximal end portion, the distal end portion extending distal of the distal open end of the stent, and the proximal end portion positioned within the interior volume; and
(b) a second balloon having a distal end portion including a distal waist portion, a proximal end portion, and an inflatable portion, wherein the first and second balloons are arranged generally coaxially, the second balloon being configured to move between:
  i. a retracted orientation wherein the inflatable portion is positioned proximal of the side branch aperture of the stent; and
  ii. an advanced orientation wherein the second balloon is advanced at least partially distally through the side branch aperture, wherein the distal waist portion extends through the side branch aperture prior to and during movement of the second balloon between the retracted orientation to the advanced orientation.

7. The stent delivery system of claim 6, wherein the second balloon is positioned on a second catheter branch and the first balloon is positioned on a first catheter branch, and the second catheter branch intersects the first catheter branch at a proximal joint, the proximal joint being located proximal of the proximal end portions of the first and second balloons.

8. The stent delivery system of claim 6, wherein the second balloon is at least partially inflated before being moved from the retracted orientation to the advanced orientation.

9. The stent delivery system of claim 6, wherein the inflatable portion of the second balloon engages the expandable structure in the advanced orientation to at least partially move the expandable structure into the radial outward orientation.

10. The stent delivery system of claim 7, wherein in the retracted position, a distal end portion of the second catheter branch extends through the side branch aperture of the stent.

11. A method of expanding a stent with a catheter assembly, the catheter assembly including a first balloon and a second balloon, the first and second balloons each including a distal end portion, a proximal end portion, and an inflatable portion, the inflatable portion of the second balloon positioned proximal of the proximal end portion of the first balloon, the distal end portion of the second balloon including a distal waist portion, the stent including a distal open end, a proximal open end, and expandable structure that defines a side branch aperture in the stent, the expandable structure being movable into a radial outward orientation, the method comprising:
(a) positioning the first balloon in a first orientation with the distal end portion of the first balloon extending distal of the distal open end of the stent and the proximal end portion of the first balloon positioned within the stent;
(b) positioning the second balloon in a retracted orientation with the proximal end portion of the second balloon extending proximal of the proximal open end of the stent, the distal waist portion extending through the side branch aperture, and the inflatable portion of the second balloon positioned proximal of the side branch aperture;
(c) at least partially inflating the second balloon; and
(d) advancing the at least partially inflated second balloon at least partially distally into an advanced orientation wherein at least a portion of the inflatable portion of the second balloon extends through the side branch aperture of the stent to move the expandable structure towards the radial outward orientation.

12. The method of claim 11, further comprising at least partially inflating the first balloon prior to advancing the at least partially inflated second balloon into the advanced orientation.

13. The method of claim 12, further comprising at least partially deflating the at least partially inflated first balloon prior to advancing the at least partially inflated second balloon.

14. The method of claim 12, wherein at least partially inflating the first balloon includes at least partially expanding a portion of the stent.

15. The method of claim 12, wherein the advancing step further includes applying an axial force to the second balloon in the distal direction upon inflation of the first balloon.

16. The method of claim 11, further comprising after advancing the at least partially inflated second balloon into the advanced orientation, further inflating the second balloon to further move the expandable structure towards the radial outward orientation.

17. The method of claim 11, wherein the catheter assembly further includes a first catheter branch and a second catheter branch, the first balloon positioned at a distal end portion of the first catheter branch and the second balloon positioned at a distal end portion of the second catheter branch, the first and second catheter branch being secured together at a location proximal of the proximal end portions of the first and second balloons, and the advancing step includes concurrently advancing the first and second balloons at least partially distally.

* * * * *